US010753901B2

(12) United States Patent
Gulak et al.

(10) Patent No.: US 10,753,901 B2
(45) Date of Patent: Aug. 25, 2020

(54) INTEGRATED SENSOR FOR THE RAPID IDENTIFICATION OF BACTERIA USING ISFETS

(71) Applicants: Glenn Gulak, Toronto (CA); Nasim Nikkhoo, Toronto (CA); Karen Maxwell, Toronto (CA)

(72) Inventors: Glenn Gulak, Toronto (CA); Nasim Nikkhoo, Toronto (CA); Karen Maxwell, Toronto (CA)

( * ) Notice: Subject to any disclaimer, the term of this patent is extended or adjusted under 35 U.S.C. 154(b) by 0 days.

(21) Appl. No.: 15/901,645

(22) Filed: Feb. 21, 2018

(65) Prior Publication Data
US 2018/0284061 A1 Oct. 4, 2018

Related U.S. Application Data

(63) Continuation of application No. 14/088,323, filed on Nov. 22, 2013, now abandoned, which is a continuation of application No. 61/729,411, filed on Nov. 22, 2012.

(51) Int. Cl.
*G01N 27/414* (2006.01)
*C12Q 1/02* (2006.01)
*C12Q 1/70* (2006.01)

(52) U.S. Cl.
CPC ........... *G01N 27/4145* (2013.01); *C12Q 1/02* (2013.01); *C12Q 1/70* (2013.01)

(58) Field of Classification Search
None
See application file for complete search history.

(56) References Cited

U.S. PATENT DOCUMENTS

2010/0282617 A1 11/2010 Rothberg

OTHER PUBLICATIONS

Totu et al., Materials Science and Engineering C, 2001, 18:87-91.
Seo, Nano Scale Devices for Plasmonic Nanolithography and Rapid Sensing of Bacteria, Dissertation, Dec. 2007.
Dreiseikelmann, Microbiological Reviews, 1994, 58(3):293-316.
Kawakami et al., Fresenius Z Anal Chem, 1984, 318:349-351.
Wong et al., IEEE Transactions on Electron Devices, 1989, 36(3):479-487.
PCT, Notification Concerning Transmittal of International Preliminary Report on Patentability, in application No. PCT/IB2013/003133, dated Jun. 4, 2015 (8 pages).
PCT, Notification of Transmittal of the International Search Report and the Written Opinion of the International Searching Authority, or the Declaration, in International application No. PCT/IB2013/003133 dated Jul. 15, 2014 (13 pages).
Nikkhoo, N., et al. "A CMOS Integrated Bacterial Sensor for Rapid Detection of Pseudomonas aeruginosa" IEEE-BIOCAS Biomedical Circuits and Systems Conference, 2008, p. 213-6.
Boulanger, P. and Letellier, L. "Characterization of Ion Channels Involved in the Penetration of Phage T4 DNA into *Escherichia coli* Cells" J. Biol. Chem. Jul. 15, 1988 (Jul. 15, 1988), V. 263(20):p. 9767-75. ISSN: 0021-9258.
Rothberg, J.M. et al. "An integrated semiconductor device enabling non-optical genome sequencing" Nature. Jul. 21, 2011 (Jul. 21, 2011), V.475,1, 348-352.
Lee, C.-S. et al. "Ion-Sensitive Field-Effect Transistor for Biological Sensing" Sensors. Sep. 2009 (Sep. 2009), V. 9(9), p. 7111-7131.
Nikkhoo, N. et al. "Rapid Detection of E.coli Bacteria Using Potassium-Sensitive FETs in 1-27 CMOS" IEEE Transactions on Biomedical Circuits and Systems. Oct. 2013 (Oct. 2013), V. 7(5), pp. 621-630.
Nikkhoo, N. et al. "Rapid Detection of *E.coli* Bacteria using Potassium-Sensitive FETs in CMOS" Proc. IEEE Biomedical Circuits and Systems Conf. Nov. 28-30, 2012 (Nov. 28, 2012 to Nov. 30, 2012), pp. 168-171.
Michael D. Scott. Student Member. IEEE, Bernhard E. Boser Fellow, IEEE, and Kristofer S. J. Pister, Member, IEEE; An Ultralow-Energy ADC for Smart Dust; IEEE Journal of Solid-State Circuits, vol. 38, No. 7, Jul. 2003; pp. 1123-1129.
Fimme Jan Van Der Wal, Joen Lui Rink, Bauke Oudega; Bacteriocin release proteins: mode of action, structure, and biotechnological application; FEMS Microbiology Reviews 17 (1995) 381-399, Received May 3 1995; revised Jul. 21, 1995: accepted Aug. 9, 1995.
Jean Paul Bourdineaud, Pascale Boulanger, Claude Lazdunski, and Lucienne Letellier; In vivo Droperties of colicin A: Channel activity is voltage dependent but translocation may be voltage independent; Proc. Natl. Acad. Sci. USA vol. 87, pp. 1037-1041, Feb. 1990 Biochemistry.
P. Bergveld; Development of an Ion-Sensitive Solid-State Device for Neurophysiological Measurements; IEEE Transactions on Bio-Medical Engineering, Jan. 1970, p. 70-71.
Suresh M. Desai and Samuel B. Weiss; Study of the Transfer RNAs Coded by T2, T4, and T6 Bacteriophages; The Journal OP Bmuxxcu. Chemistry vol. 252, No. 14, Issue of Jul. 25. pp. 4935-4941, 1977.

(Continued)

*Primary Examiner* — Nicole Kinsey White
(74) *Attorney, Agent, or Firm* — McAndrews, Held & Malloy, Ltd.

(57) ABSTRACT

Disclosed are methods and systems for the detection of bacteria in a sample. The methods comprises contacting the sample with an antibacterial agent and a bacteria identification sensor, and involves the permeabilization of the bacteria by the antibacterial agent, and the subsequent detection of an efflux of potassium ions using a bacteria identification sensor comprising a potassium-sensitive ISFET. Also disclosed are bacteria identification sensor comprising a potassium-sensitive ISFET useful in the practice of the disclosed methods.

24 Claims, 13 Drawing Sheets

(56) References Cited

OTHER PUBLICATIONS

U. Fiedler, J. Ruzicka; Selectrode—The Universal Ion-Selective Electrode; Analytica Chimica Acta, 67 (1973) 179-193.
Llenado, "Potentiometric Response of the Calcium Selective Membrane Electrode in the Presence of Surfactants", Analytical Chemistry, vol. 47 No. 13, Nov. 1975, 2243.

US 10,753,901 B2

INTEGRATED SENSOR FOR THE RAPID IDENTIFICATION OF BACTERIA USING ISFETS

RELATED APPLICATIONS

This application claims priority to non-provisional application Ser. No. 14/088,323 filed Nov. 22, 2013, which is related to and claims priority from U.S. provisional Application No. 61/729,411 having a filing date of Nov. 22, 2012, both in which are incorporated herein by reference in their entirety.

This application also incorporates herein by reference in their entirety the following applications: Provisional Application No. 61/878,021, filed on Sep. 15, 2013 and Provisional Application No. 61/749,368, filed on Jan. 6, 2013.

FEDERALLY SPONSORED RESEARCH AND DEVELOPMENT

[Not Applicable]

MICROFICHE/COPYRIGHT REFERENCE

[Not Applicable]

BACKGROUND OF THE INVENTION

There is increasing demand for systems that detect bacteria with good selectivity and sensitivity, in applications ranging from medical diagnosis to water and food inspection. Traditional culturing methods take several hours to days to give results. They require trained personnel to perform the tests as well as expensive laboratory equipment. Techniques using DNA amplification and detection, such as those employing the polymerase chain reaction (PCR), provide results over several hours.

DNA-based detection approaches offer the potential for miniaturization and have been integrated on silicon chips. The disadvantages of these methods are laborious sample preparation. More importantly, these methods primarily do not distinguish between living and dead bacterial cells.

Further limitations and disadvantages of conventional and traditional approaches will become apparent to one of skill in the art, through comparison of such approaches with some aspects of the present method and apparatus set forth in the remainder of this disclosure with reference to the drawings.

BRIEF SUMMARY OF THE INVENTION

A system and/or method for an integrated sensor for the rapid sensing of bacteria using ion-sensitive field effect transistors (ISFETS), substantially as shown in and/or described in connection with at least one of the figures, as set forth more completely in the claims.

Various advantages, aspects and novel features of the present invention, as well as details of an illustrated embodiment thereof, will be more fully understood from the following description and drawings.

DETAILED DESCRIPTION OF THE INVENTION

The present disclosure includes a bacteria identification sensor integrated in CMOS using bacteriophages (phages) as biological sensing elements combined with ion-selective FETs (ISFET) implemented in conventional CMOS technology to accurately detect specific strains of living bacteria in shorter times, for example less than 30 minutes. The present technology employs sensitive low-noise electronic circuits combined with biological sensing elements (e.g., bacteriophages) to provides, among other things, a simple low-cost platform for the detection of bacteria, and the specificity required to sense different strains of living bacterial cells accurately. Other antimicrobial agents that result in bacteria cell wall permeabilization can be used instead of phages. The present technology can be used to test the effectiveness of antibacterial agents in samples. Traditionally, ISFETs in conventional processes are not used for ion concentration measurements because of non-idealities like drift. The presented system shows that they can be effectively used in applications like bacteria detection.

Figure 1:
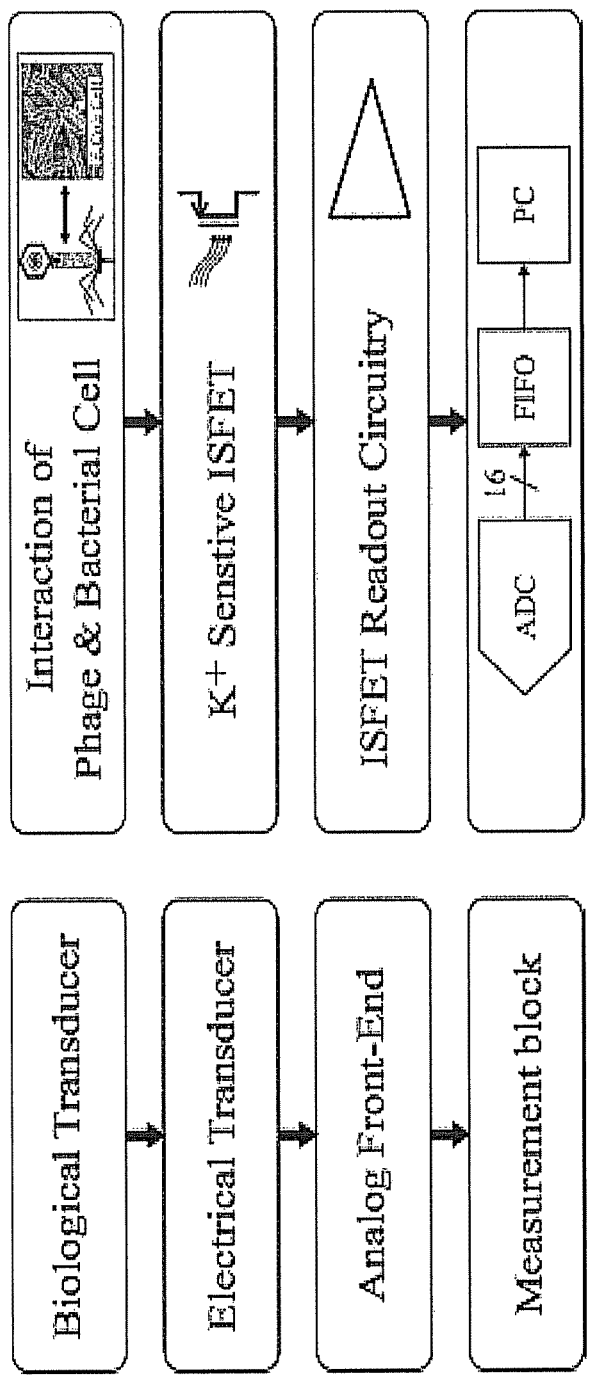
FIG. 1 illustrates four building blocks of the bacterial sensor system, in accordance with an example embodiment of the disclosure.

The bacterial sensor system, or bacteria identification sensor, is generally comprised of four building blocks as detailed in FIG. 1. The biological transducer generates the detectable signal in the electrical transducer. It consists of the test sample plus phages specific to a particular bacterial cell. The output signals from this block are the released potassium ions in the sample that need to be converted into an electrical signal using the electrical transducer (ISFET) block. The analog circuitry that reads the signal from the electrical transducer is the analog front-end whose output is then converted to a digital representation by an analog-to-digital converter. The digital output is transferred to a PC or a microprocessor and is further processed, stored and/or visualized.

In some embodiments, integrated sensor may be fabricated using a silicon-based implementation. In addition, in some embodiments, standard CMOS technology may be used. In an example scenario, some or all of the various blocks shown in FIG. 1 may be integrated on a CMOS chip. For example, along with the potassium-sensitive ISFET, the readout circuitry, analog-to-digital converter (ADC), and associated processing circuitry may also be integrated on chip, and coupled by wire or wirelessly to external devices, such as a computer or other test equipment.

In some embodiments, integrated sensor may be fabricated in a substrate selected from the group consisting of silicon, plastic, polymer, glass, sapphire, quartz, carbon, silica, silicon carbide, zinc oxide, magnesium oxide, manganese oxide, germanium, gallium nitride, gallium arsenide, gallium phosphide, indium phosphide, polysilicon, n-type diffusion semiconductor material, and p-type diffusion semiconductor material.

In some embodiments, some or all of the various blocks shown in FIG. 1 may be integrated using combinations of CNTs, FETs, JFETs, MOSFETs, OSFETs, FinFETs, bipolar transistors, amorphous silicon TFTs, plastic transistors and organic transistors.

Figure 2:
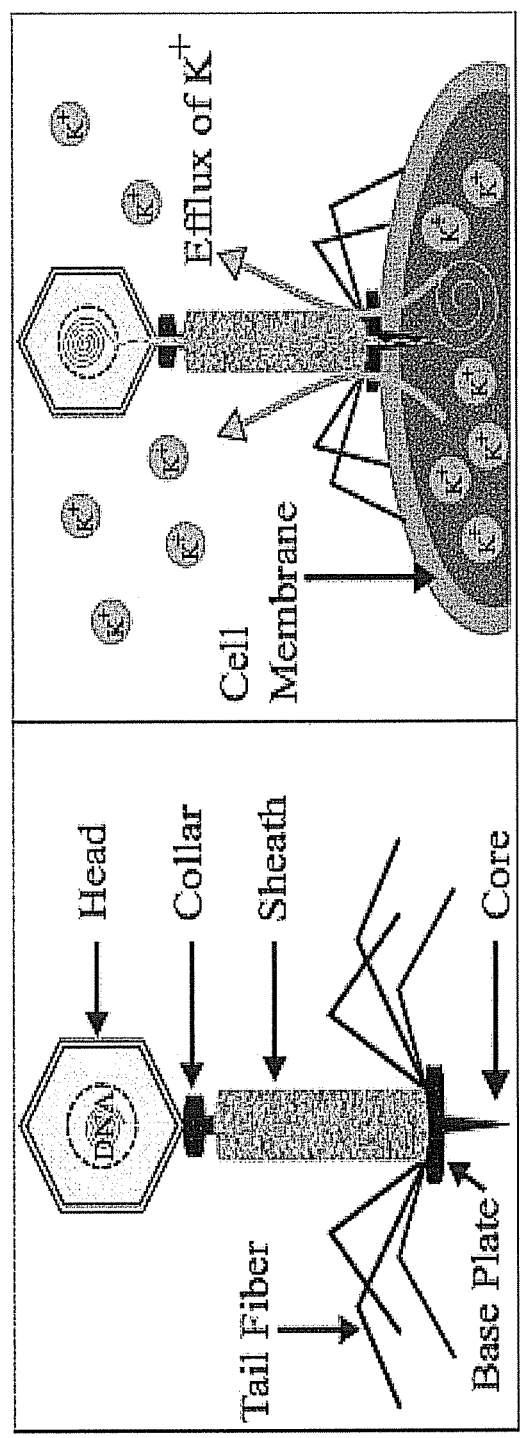
FIG. 2 illustrates a bacteriophage and its interaction with a target bacteria cell, in accordance with an example embodiment of the disclosure.

Generally, detection of specific strains of bacterial cells can be achieved using bacteriophages that infect that strain. The interaction between the phage tail fibers and receptors on the bacterial cell surface results in attachment of the phage to the bacterial cell. After phage attachment, the cell membrane goes through a depolarization phase and becomes permeable to specific ions especially potassium ions. Phage DNA is transferred from the head part of the phage to inside the cell. Following this phase there is an efflux of ions from inside the cell to the media outside the cell as shown in FIG. 2. Potassium ions are the dominant ions inside the cell that flow to the outside sample as a result of phage infection. This transient efflux of K+ is used as the signal to be detected in an electrical transducer using potassium sensitive ISFETs.

Examples of bacteria that may be detected using methods and devices according to the present invention include both Gram-positive and Gram-negative bacteria such as members of the genera *Acinetobacter, Burkholderia, Escherichi, Legionella, Borrelia, Helicobacter, Parachlamydia, Bacteroides, Coxiella, Ehrlichia, Pasteurella, Porphyromonas,* and *Rickettsia, Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus* and *Bordetella*

Examples of bacteriophage that may be used in the practice of the present invention include libraries of Siphoviridae, Myoviridae, and Podoviridae, including those available in the American Type Culture Collection (ATCC) and those isolated from relevant bacterial strains. Phages engineered for both broad and narrow host ranges by swapping, fusing, or otherwise manipulating the host-specificity determinants encoded in the tail proteins. Other examples include *S. mutans* phages, *Bacillus* phage PHI.29, *Actinomyces* phages, bacteriophage M102, bacteriophage e10, bacteriophage f1, bacteriophage lamda., bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, and ssRNA bacteriophages Q beta. Phage libraries are available in collections of the American Type Culture Collection (ATCC).

In various embodiments phage tail-like bacteriocins (PTLB), ghost phages, antimicrobial peptide, bacterial lytic enzymes, bacteriophage lytic enzyme and antibiotics can be used instead of phages to generate an efflux of ions. Phage ghosts are the viral protein shell from which the genome has been extracted. Examples of phage ghosts include those prepared from the Siphoviridae, Myoviridae, and Podoviridae families Examples of bacteriophage lytic enzymes include various bacteriocins. bacteriophage lytic enzymes include lytic agents produced by bacteriophages infecting Gram-positive and Gram-negative bacteria.

Examples of lytic enzymes (bacterial and bacteriophage based) can be found in databases of curated bacteriocins and lysins (e.g., BAGEL2, BACTIBASE, phiBIOTICS, EnzyBase). Examples of bacteriocins include acidocin, actagardine, agrocin, alveicin, aureocin, aureocin A53, aureocin A70, carnocin, carnocyclin, colicin, curvaticin, divercin, duramycin, enterocin, enterolysin, epidermin/gallidermin, erwiniocin, glycinecin, halocin, haloduracin, Lactocin S, lysostaphin, lactococcin, lacticin, leucoccin, macedocin, mersacidin, mesentericin, microbisporicin, Microcin S, mutacin, nisin, paenibacillin, planosporicin, pediocin, pentocin, plantaricin, pyocin, reutericin, sakacin, salivaricin, subtilin, sulfolobicin, thuricin 17, trifolitoxin, variacin, vibriocin, warnericin, warnerin.

Phage tail-like bacteriocins (PTLBs or Tailocins) are high molecular weight bacteriocins that are evolutionarily related to phage tails. Examples include R- and F-pyocins, Diffocin, Enterocoliticin, and Carotovoracin.

Bacteriocidal antibiotics include, for example, Polymyxins, Colistins, Gramicidins, Neomycin, Vancomycin, Daptomycin, Telavancin, DCAP and HT61.

The outputs of the biological transducer are the potassium ions. For example, the level of potassium build-up after the addition of bacteriophage to a sample is proportional to the concentration of the present infected bacterial cells. CMOS-based ISFETs are the ideal transducers for sensing a specific ion in the sample. They offer rapid response time, small size and can be integrated along with other required readout and signal processing circuitry on the same integrated circuit or chip; hence low noise and small form-factor systems can be implemented with multiple measurement channels.

Figure 3:
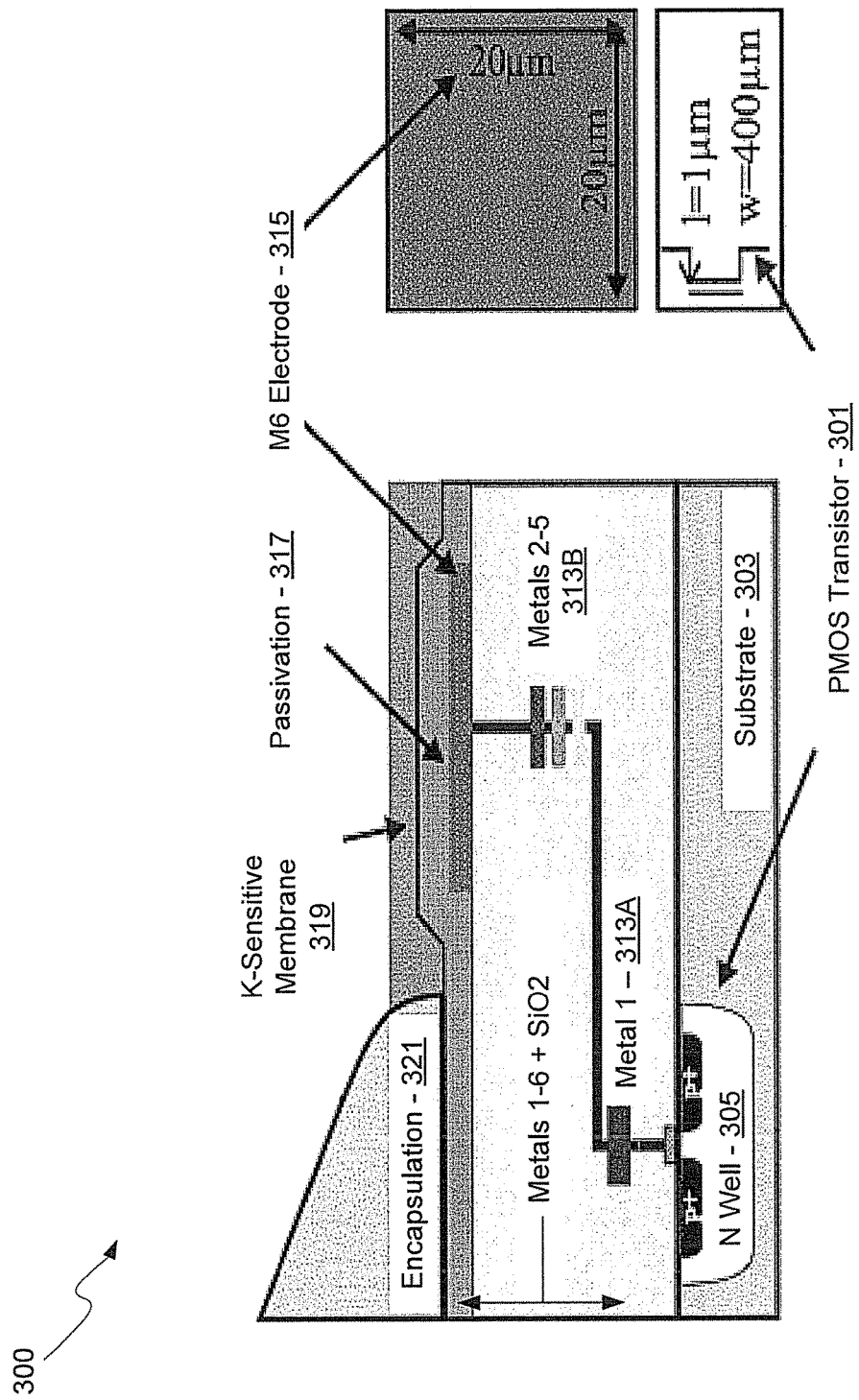
FIG. 3 shows a block diagram of a potassium-sensitive system on chip, in accordance with an example embodiment of the disclosure.

FIG. 3 is a block diagram of a potassium-sensitive system on chip, in accordance with an example embodiment of the disclosure. Referring to FIG. 3, there is shown a chip 300 comprising p-channel metal-oxide semiconductor (PMOS) transistors, such as the PMOS transistor 301, integrated on the chip 300, with its gate connected through vias and multiple levels of metal, such as the metal layers 1-6, to the top metal layer, the M6 electrode 315. In an example scenario, the PMOS transistor 301 may have a width/length ratio of 400/1. In an example scenario, the PMOS transistor 301 maybe substituted (with appropriate circuit modifications) by an NMOS transistor. In an example scenario, NMOS or PMOS transistor may have other width/length ratios.

The PMOS transistor 301 may be formed in the substrate 301, which may comprise a silicon CMOS wafer or a silicon-on-insulator (SOI) wafer, for example. Metal and insulating layers such as the metal layers 313A and 313B and passivation layer 317, respectively may be formed on top of the CMOS transistors, such as the PMOS transistor 301, on the substrate 303, for connecting the devices to external contacts, such as the M6 electrode 315, which may comprise a 20.times.20 um pad, for example.

In an example scenario, the passivation layer 317 on top of the top metal, M6 electrode 315, may comprise a mixture of SiO.sub.2 and Si3N.sub.4, for example, which may be suitable for pH sensors (H+ ions). In order to achieve the desired potassium sensitivity (e.g., K+ ions), a potassium sensitive membrane 319 may be prepared and deposited on top of the chip 300.

In an example scenario there may be no passivation layer and only a top metal layer (e.g. M6 electrode 315). In order to achieve the desired potassium sensitivity (e.g., K+ ions), a potassium sensitive membrane 319 may be prepared and deposited on top of the chip 300 directly touching the top Metal electrode 315.

In an example scenario there maybe one or several intermediate layers deposited on top metal layer (e.g. M6 electrode 315). In order to achieve the desired potassium sensitivity (e.g., K+ ions), a potassium sensitive membrane 319 may be prepared and deposited on top of the intermediate layers other than passivation layer.

In an example scenario, the passivation layer 319 or some intermediate layer on top metal (e.g. M6 electrode 315) can be made potassium sensitive by methods other than deposition.

The encapsulation layer 321 may comprise an epoxy encapsulant, or parylene or other suitable material, for protecting portions of the chip 300, while not covering portions to be used in sensing ions, such as the potassium sensing membrane 319. The material for the encapsulation layer 321 may be chosen based on what chemical compounds it will be exposed to in operation.

While a single CMOS transistor and potassium-sensitive membrane are shown in FIG. 3, any number of transistors and membranes may be integrated on the chip 300. For example, multiple transistors, each with different ion-sensitive membranes may be integrated, providing sensitivity to multiple types of bacteria or ions. Similarly, different size membranes may be coupled to CMOS transistors for possible concentration measurements.

Figure 9:
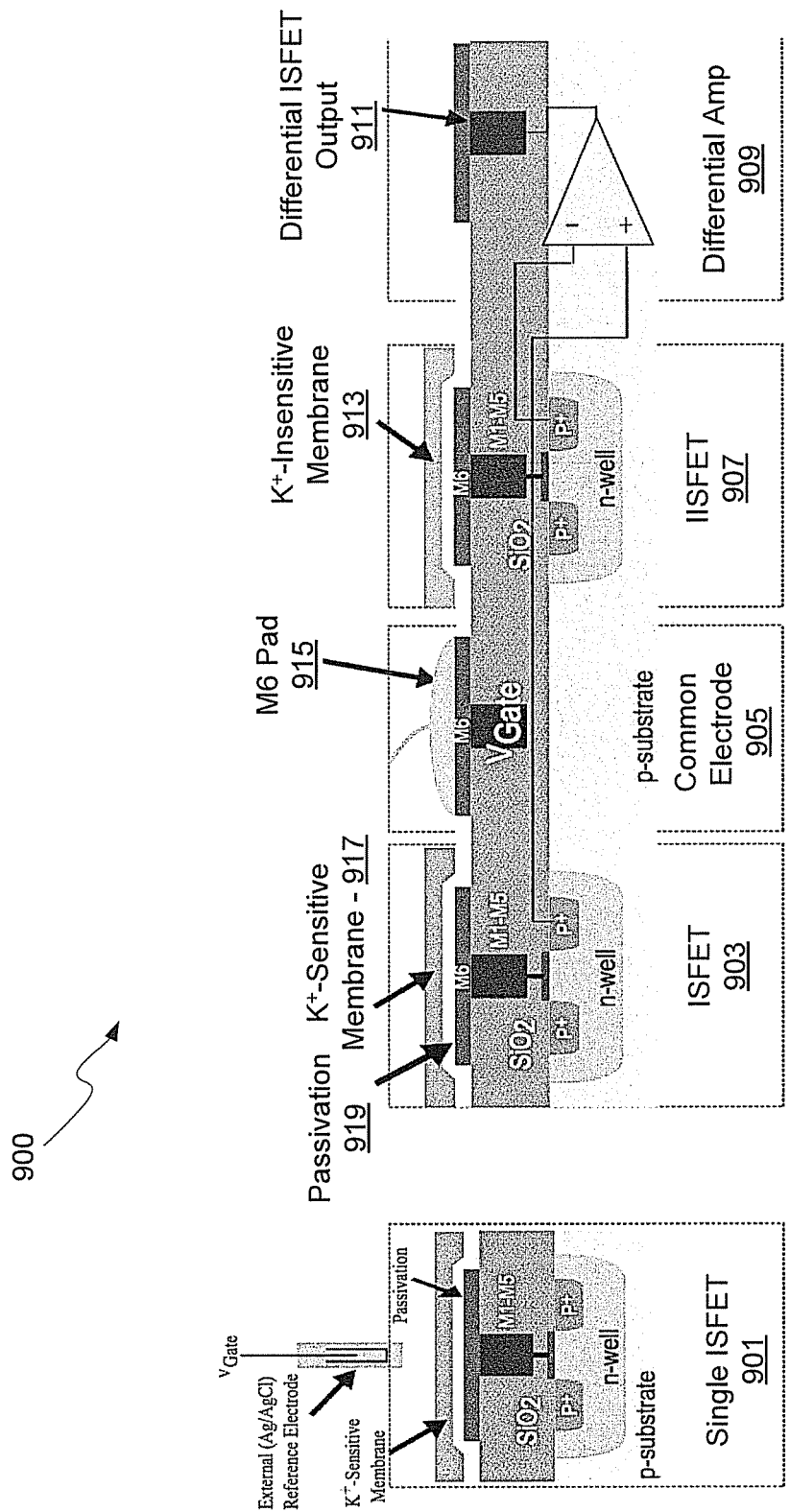
FIG. 9 illustrates a differential ion sensitive field effect transistor circuit, in accordance with an example embodiment of the disclosure.

Furthermore, CMOS transistors may be coupled in a differential configuration with one coupled to a ion-sensitive membrane and another to an ion-insensitive membrane, as shown in FIG. 9. In an example scenario, both outputs may be connected to difference amplifiers to measure the difference between the signals. This configuration makes the system completely integrated without the use of external reference electrodes or non-standard integration of reference electrodes and also improves common-mode noise and compensation for circuit and system non-idealities.

In an example scenario, the potassium-sensitive membrane 319 may comprise a macrocyclic substance from a group of depsipeptides, such as valinomycin, as the ion-exchanger. This antibiotic forms complexes with alkali metal ions and is highly selective to potassium K+ ions, and is a member of group of natural neutral ionophores.

Figure 4:
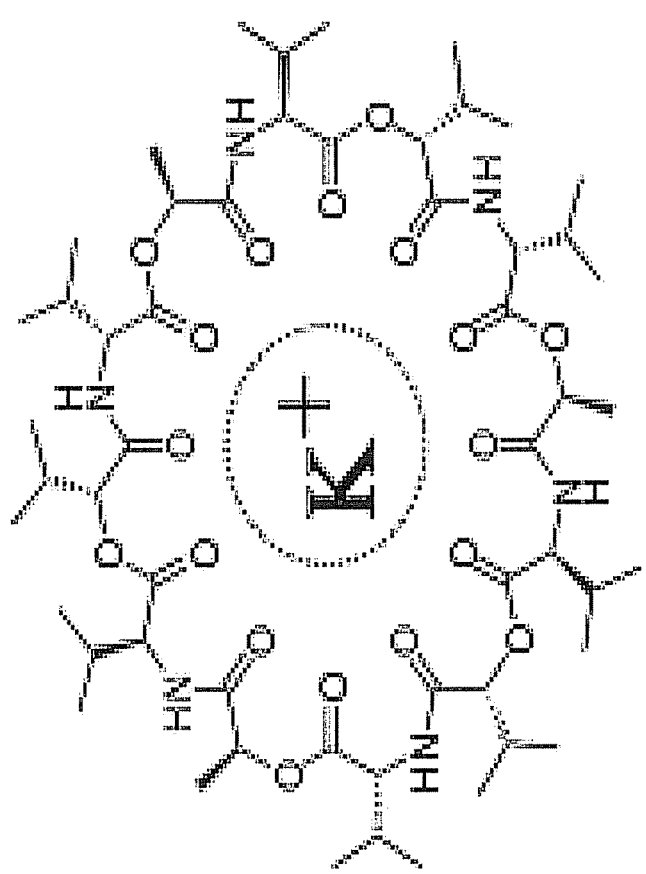
FIG. 4 illustrates the structure of valinomycin with a potassium ion held inside the cylinder, in accordance with an example embodiment of the disclosure.

FIG. 4 shows the structure of the valinomycin, where the potassium ion is held inside the cylinder that fits the size of K+ ion. The ion-exchanger is dissolved in an organic solvent like tetrahydrofuran (THF) along with polyvinylchloride (PVC) and plastizer dioctylphthalate that together build a porous membrane to hold the valinoymicin inside the membrane structure.

In order to enhance the attachment of the membrane to the chip surface, surface cleaning, drying and silanization may be performed as follows. The encapsulated chip may be cleaned using acetone and isopropanol and then deionized water. The chip may be dried using nitrogen gas and placed in an oven at 110 C. After further drying at room temperature, a small droplet of Microprimer P20 (ShinEtsu MicroSi) may be deposited on the surface of the chip as an adhesion promoter under the fumehood. After drying of the promoter, droplets of the membrane solution may be dispensed on top of the electrodes 2 to 3 times with 5-minute intervals in between applications to create a smooth membrane layer with a thickness in the range of 100 to 300 .mu.m without any pinholes. The membrane may be left to dry (at room temperature) for several hours. This process results in a K+ sensitive ISFET as the electrical transducer.

Figure 5:
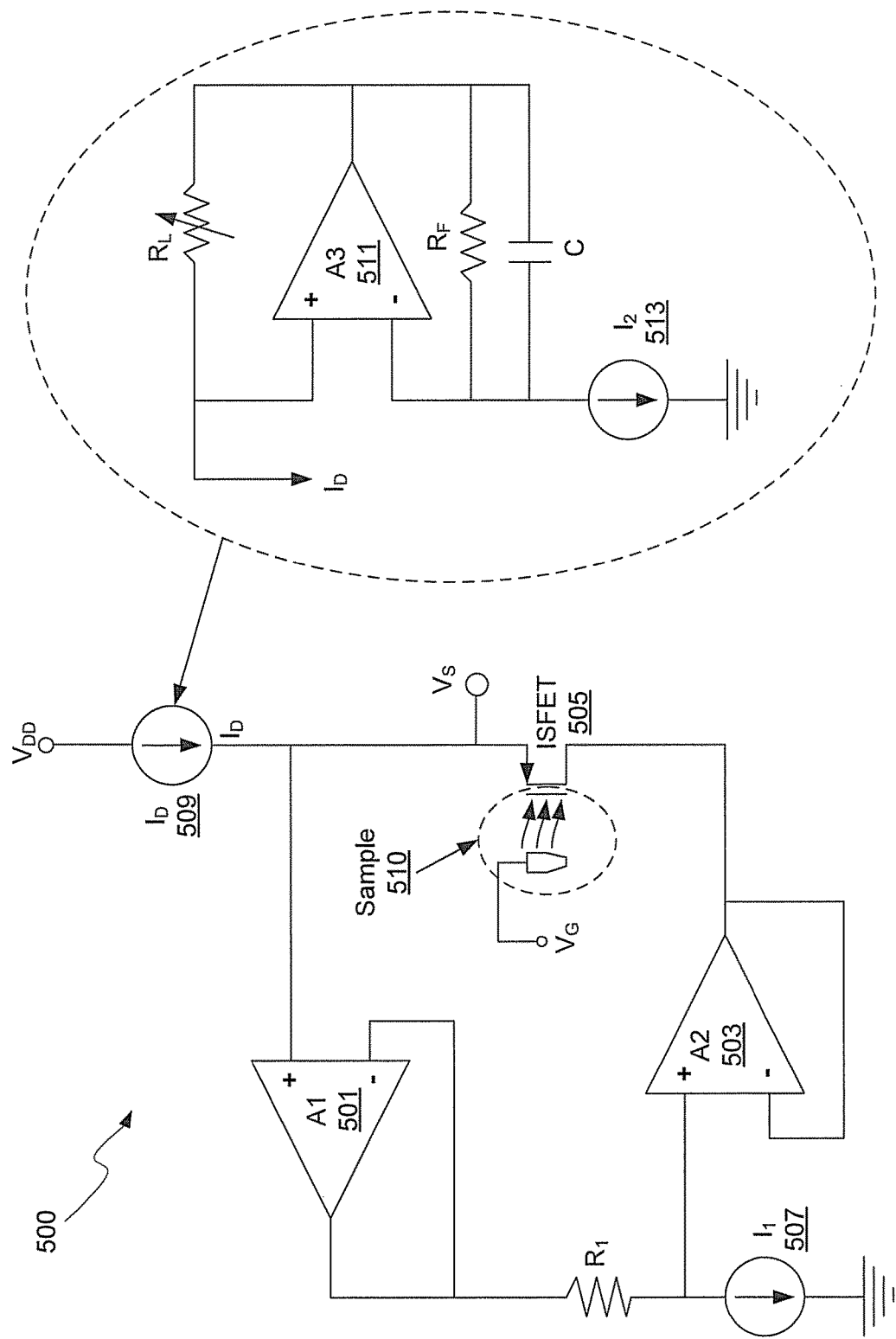
FIG. 5 is a diagram of an ion sensitive field effect transistor bias and readout circuit, in accordance with an example embodiment of the disclosure.

FIG. 5 is a diagram of an ion sensitive field effect transistor bias and readout circuit, in accordance with an example embodiment of the disclosure. Referring to FIG. 5, there is shown ISFET circuit 500 comprising a drain-source follower arrangement used to read the ISFET threshold variations. The ISFET 505 may comprise a PMOS FET with ion sensitive membrane, as described with respect to FIG. 3.

ISFET circuit 500 comprises current sources for controlling the bias conditions for the ISFET 505, which may be in contact with a sample 510. For example, current source ID 509 may be operable to control the bias current of the ISFET 505. The inset to the right in FIG. 5 is a schematic of the current source ID 509, comprising an operational amplifier (op amp) A3 511, a feedback resistor RF, feedback capacitor C, a variable load resistor RL, and a current source I2 513. In an example scenario, the load resistor RL may have a resistance that is a multiple N times the resistor R1.

In addition, the op amps A1 501 and A2 503 may be operable to control the drain-source voltage (VDS) of the ISFET 505. In this example scenario, with the outputs of the op amps 501 and 503 tied to the inverting inputs, the op amps act to keep the voltage difference between their inputs at zero, so that the output tracks with the non-inverting inputs. Thus, by adjusting the current source I1 507, the outputs of the op amps 501 and 503 essentially define the source and drain voltages, i.e., VDS.

In operation, both VDS and drain current (ID) of the ISFET may be fixed to 0.5 volts and 100 .mu.A, respectively. A fixed DC voltage (VG) may be applied to the solution being in contact with the ISFET 505 using a reference electrode in the solution. The source voltage (VS) of the ISFET may be measured using a readout circuit, which may be integrated on the chip comprising the ISFET 505 or may be external to the chip.

The gate source voltage, VGS, of the PMOS ISFET 505 may be defined by the process parameters of the transistor when a fixed drain-source voltage, VDS, and drain current ID are applied. The changes in the threshold voltage of the ISFET 505, because of K+ concentration variations placing a charge on the gate terminal of the ISFET 505, may be reflected in the source voltage, VS. As the concentration of K+ increases, VS may also increase. For testing purposes, both current ID and VDS of the ISFET 505 may be variable to enable complete ID-VDS characterization curves.

Figure 6:
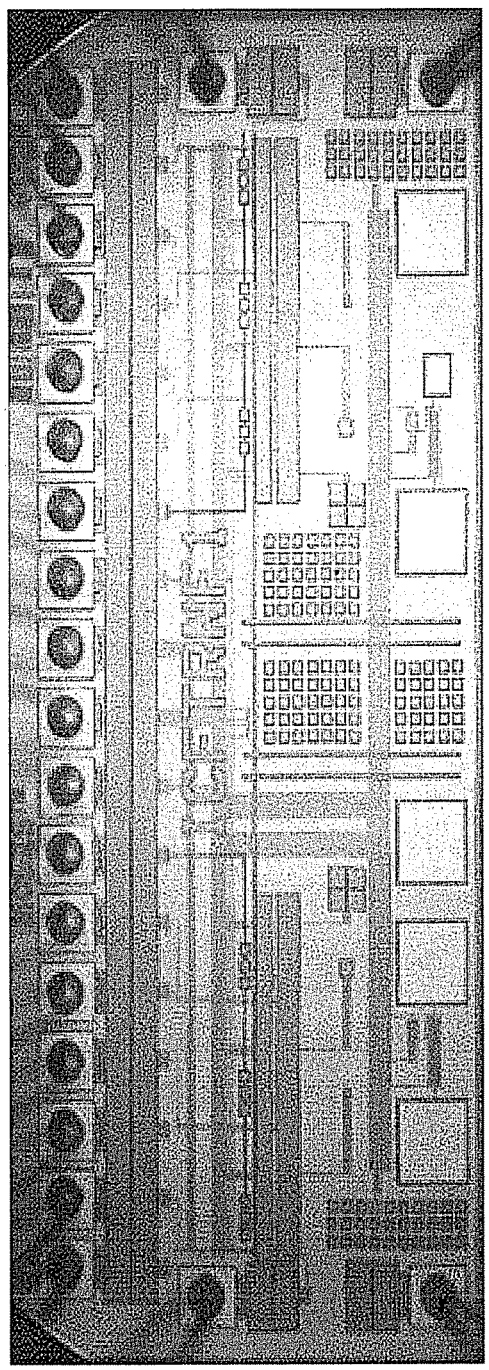
FIG. 6 is a photograph of a die comprising ion sensitive field effect transistors and associated readout circuitry, in accordance with an example embodiment of the disclosure.

FIG. 6 is a photograph of a die comprising ion sensitive field effect transistors and associated readout circuitry, in accordance with an example embodiment of the disclosure. Referring to FIG. 6, there is shown an ISFET system 600 implemented in a standard 0.18.mu.m CMOS technology. The implemented 0.18.mu.m CMOS chip die photo is shown in FIG. 6. This chip contains several measurement channels with different sized electrodes as well as other test circuitry. Outputs of the ISFET readout circuits were converted to a digital representation and transferred to a PC using a data acquisition board and visualized real-time using lab system monitoring software. However, since the ISFETS may be integrated in conventional CMOS circuits, much of the processing and readout circuitry may be integrated on the sensor chip, as opposed to external boards and systems. For example, ultra-low power analog-to-digital converters (ADCs) may be integrated on-chip.

In the following examples, the chip or chips may be encapsulated to isolate the bond wires from the sample, leaving only the electrodes exposed.

The Examples that follow are intended to be illustrative of the aspects and embodiments described above. Neither the above disclosure nor the Examples below should be viewed as limiting to the scope of the appended claims. One of skill in the art will appreciate that the disclosure is not limited by the particular terminology which is used to describe and illustrate the various aspects of the disclosure.

Example 1

Live bacterial cells and phages were used on the chip in demonstration of the ISFET system 600. Before starting the experiments, the chips may be cleaned and potassium-sensitive ISFET chips prepared as explained in the previous sections.

The measurements were done using two strains of like *E. coli* K-12 bacterial cells. The positive control experiments were performed using *E. coli* K-12 BL21 (DE-.DELTA.tail), called BL21 here for simplicity, which are sensitive to phage T6. The negative control experiments were performed using bacterial cells *E. coli* K-12 BW25113 with TSX-, called TSX- here, which are insensitive to phage T6. The phages used throughout the experiments were T6 phages.

Bacterial cultures were prepared overnight using frozen cultures inoculated in luria broth (LB) growth media. The overnight cultures were then inoculated to make fresh samples to be used the same day. The growth of the cells was monitored using a spectrophotometer that read the optical density (OD) of the samples compared to a blank LB sample. For both experiments, cultures were used as their OD reached 1.2, which translates to a cell concentration of approximately 10.sup.9 cfu/ml. After growth, the bacteria were washed and resuspended twice in a clean media without potassium where they would remain alive without replication.

The T6 phages were prepared beforehand and can be stored at 4.degree. C. for several months without any drop in their concentration (i.e. titer). The concentration of phages used in the experiments was 8.times.10.sup.10 pfu/ml.

Figure 7:
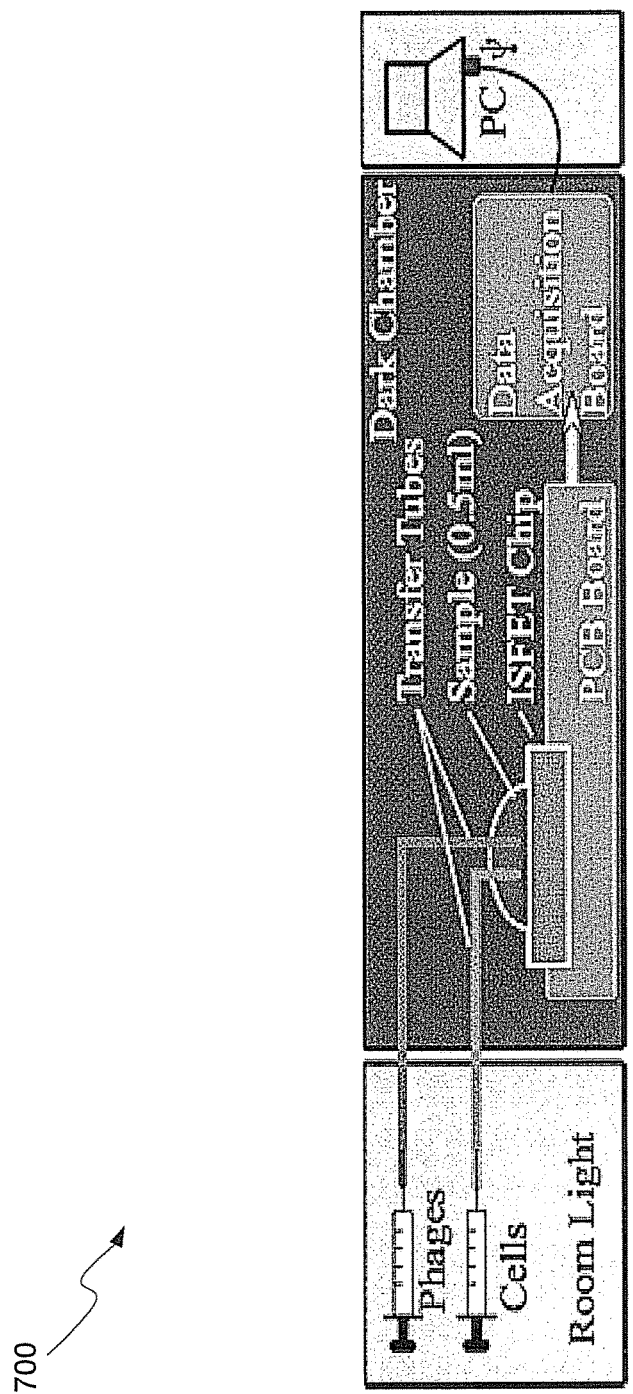
FIG. 7 shows the block diagram of an experimental setup for sensing the presence of bacteria cells, in accordance with an example embodiment of the disclosure.

Because ISFETs are sensitive to light, measurements were performed inside a dark chamber. The cells and bacteriophage were transferred to the top surface of the chip via tubes connected to their respective syringes outside the dark chamber. The syringes were manipulated manually for transfer and mixing of the cells and phages. FIG. 7 shows the block diagram of the setup.

Two sets of experiments were performed using BL21 and TSX- cells, respectively. A positive control experiment was performed by mixing the BL21 cells with T6 phages. BL21 cells are sensitive to T6 phage and infection and release of potassium will proceed after mixture. A negative control experiment was performed by mixing the TSX- cells with T6 phages. TSX- cells are insensitive to T6 phages; hence no infection and no potassium release is expected. At the beginning of each experiment, 0.5 ml of the bacterial cells (BL21 for positive control and TSX- for negative control) were transferred to the ISFET chip surface and the measurement started. ISFET outputs were recorded for 5 minutes without addition of the phages. This step can help identify the ISFET drift and obtain a DC baseline in the measurements. After 5 minutes, 204, of T6 phages were added to the sample and mixed thoroughly for 1 minute. The mixture was left on the chip for 30 minutes. Data was continuously recorded from the start of the measurement, through the mixing phase and also after mixing until the end of the experiment. The results shown in FIG. 8 were processed in Matlab with a 0.3 Hz low-pass filter. The results show .DELTA.V changes to remove any DC baseline differences between the experiments. ISFETs are known to have inferior drift and hysteresis problems compared to ISE counterparts. In this detection scheme, since the potassium level changes are measured before and after the addition of the phages, drift or hysteresis and threshold voltage variations between ISFETs do not interfere with results and can be disregarded or post processed from the measurement data. Here the DC baseline has been removed, but drift is present and shown in FIG. 8.

Figure 8:
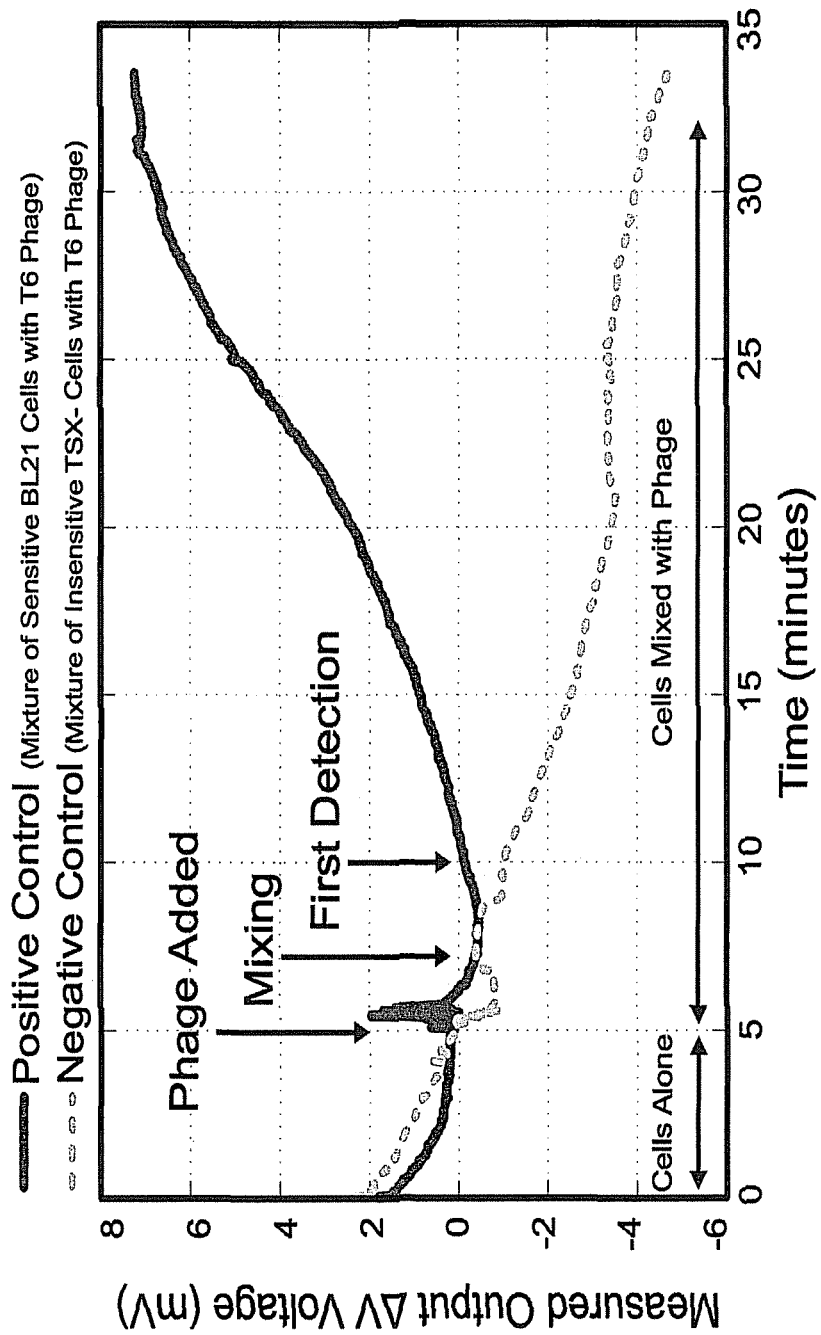
FIG. 8 shows experimental results of both positive and negative control experiments using the bacteria sensing system, in accordance with an example embodiment of the disclosure.

FIG. 8 shows the results of both positive and negative control experiments. As shown, the output increases as a result of the efflux of potassium ions from the live infected cells in the positive control test. In the negative control experiment, the output continues to have the downward ISFET drift similar to that present before the addition of the phages.

The results indicate that the integrated potassium-sensitive chip can detect the presence of a specific *E. coli* strain BL21 using the bacteriophage T6. The designed sensor system can tolerate the non-idealities present in ISFET integrated circuits like drift, hysteresis and threshold variations without affecting the results. Simple signal processing circuitry can be added to enhance analysis and visualization. Post-processing circuitry can readily be integrated on-chip to indicate the detection of the target bacteria (present/not-present) in less than 30 minutes. Inspection of the measured results confirm that the detector outcome can accurately be determined within the first 10 minutes after mixing the bacteria and phage.

An integrated ISFET chip provides an integrated lab-on-chip solution for the rapid identification of live bacteria. It combines the specificity of phages, as well as other appropriate antibacterial agents, as the biological detecting elements and the sensitivity afforded by ISFET and CMOS circuitry implemented in conventional CMOS technology whose electrodes are post-processed with a potassium-sensitive membrane. The implemented system along with measurement results show that the system can be exploited to achieve a low-cost, portable bacterial identification system. Non-idealities such as drift in ISFETs have no material effect on the integrity of collected data affording a detection time of less than 30 minutes.

In addition, further steps may be taken to integrate the system further and make it more portable. For example, in some embodiments, a micro-fluidic package may be added to transport the bacteria sample to the electrodes. More specifically, in some embodiments, micro-fluidic channels could be used to guide fluid to the measurement site that contains the electrodes. The use of such channels can prevent the liquid from spilling out into areas other than the test site and from contaminating the environment outside of the chip. This may be particularly advantageous when the fluid sample may contain dangerous bacteria.

Although the description above focused on the use of a particular phage and bacterium, it is not intended to exclude the use of other phages or bacteria. For example, lambda cI857Sam7 phage can be combined with *E. coli* w3110.DELTAlhuA as the positive control, and lambda cI857Sam7 phage can be combined *E. coli* w3110.DELTA.lamB as the negative control. Moreover, it is not intended to exclude other appropriate antibacterial agents that may kill, destroy or incapacitate bacteria by, for example, attacking their cell walls. Appropriate antibacterial agents may include, but are not limited to, phage ghosts, phage tail-like bacteriocins (PTLBs), antimicrobial peptides, bacteriophage lytic enzymes, and bactericidal antibiotics.

Phage ghosts are bacteriophage particles that are lacking nucleic acid. These particles have the ability to depolarize the cell membrane and cause leakage of ions out of the cell. Phage ghosts may potentially be generated from any phage particle by knocking the DNA out of the head by, for example, but not limited to treating with EDTA.

Antimicrobial peptides are short proteins that are naturally produced or chemically synthesized and exhibit a range of activities, including solubilization of the bacterial cell membrane. They are useful against Gram-positive and Gram-negative bacteria.

Each chip may be prepared prior to testing a sample of bacteria by applying an appropriate antibacterial agent to the testing site (electrodes of the ISFETs). For example, but not limited to, the antibacterial agents mentioned above may be applied and/or immobilized to the electrodes.

Sensor according to the present invention can be used at clinics or hospitals in order to quickly determine the effectiveness of a particular antibacterial agent in killing a bacterium causing an infection in a patient. Alternatively, the sensor can be used at clinics or hospitals in order to quickly identify the type of bacterium or bacteria causing infections in a patient. In either case, the healthcare professional(s) can quickly (on site) identify a specific and targeted treatment for the infection, in a much faster time frame as compared to sending a sample to a laboratory for analysis. Once this determination has been made, a very specific antibiotic could be selected instead of a broad-spectrum antibiotic, which may cause other bacteria to be killed. For example, in the case of an infection in a patient's gastrointestinal tract, it may be desirable to treat the patient with a very specific and targeted antibiotic as opposed to a broad-spectrum antibiotic in order to avoid killing bacteria that are beneficial to the health of the patient.

FIG. 9 illustrates a differential ion sensitive field effect transistor circuit, in accordance with an example embodiment of the disclosure. Referring to FIG. 9, there is shown a single ISFET 901, similar to the ISFET shown in FIG. 3, and a differential ISFET configuration comprising the ISFET 903, a common electrode 905, an ion-insensitive FET (IISFET) 907, and a differential input amplifier 909.

The ISFET 903 may be substantially similar to the previously described ISFETS with a potassium sensitive membrane 917, while the IISFET 907 may comprise a potassium ion insensitive membrane 913, making it an ion in-sensitive FET, or IISFET. The CMOS transistor portions of the ISFET 903 and the IISFET 907 may be essentially identical due to the uniformity provided by adjacent devices fabricated in a CMOS process.

The M6 pad 915 may comprise an external connection, via a wire bond, for example, to the common electrode 905, which may replace the external reference electrode for the sample being measured by applying a gate voltage, as illustrated by the voltage $V_G$ in FIG. 3.

By utilizing the ISFET 903 with the IISFET 907, where the CMOS transistors are in close proximity and the devices are nearly identical, any measurement changes due to drift or non-linearity may be canceled due to the differential configuration. In addition, the common electrode 905 eliminates the need for a separate electrode for each ISFET in an array. The difference between the two signals may then be amplified by the differential amplifier 909, where the output signal may be read from the differential ISFET output 911.

In addition, arrays of ISFET/IISFET differential pairs may be integrated on chip with varying sizes of M6 pads as well as different ion-sensitive membranes, enabling the sensing of a variety of bacteria and even the concentration of the bacteria.

Example 2

This example demonstrates that bacteriocins can be used to detect the presence of a bacterium in a sample using methods and devices according to the present disclosure. In this example, the bacteriocin Colicin A9 was combined with *E. coli* K12 BW25113 as the positive control. As negative controls, Colicin A9 was combined with *Staphylococcus aureus* 8325, and Colicin A9 was combined with *Pseudomonas aeruginosa* (PA01). Experiments were performed as described above for Example 1, using the ISFET system 600.

Figure 10:
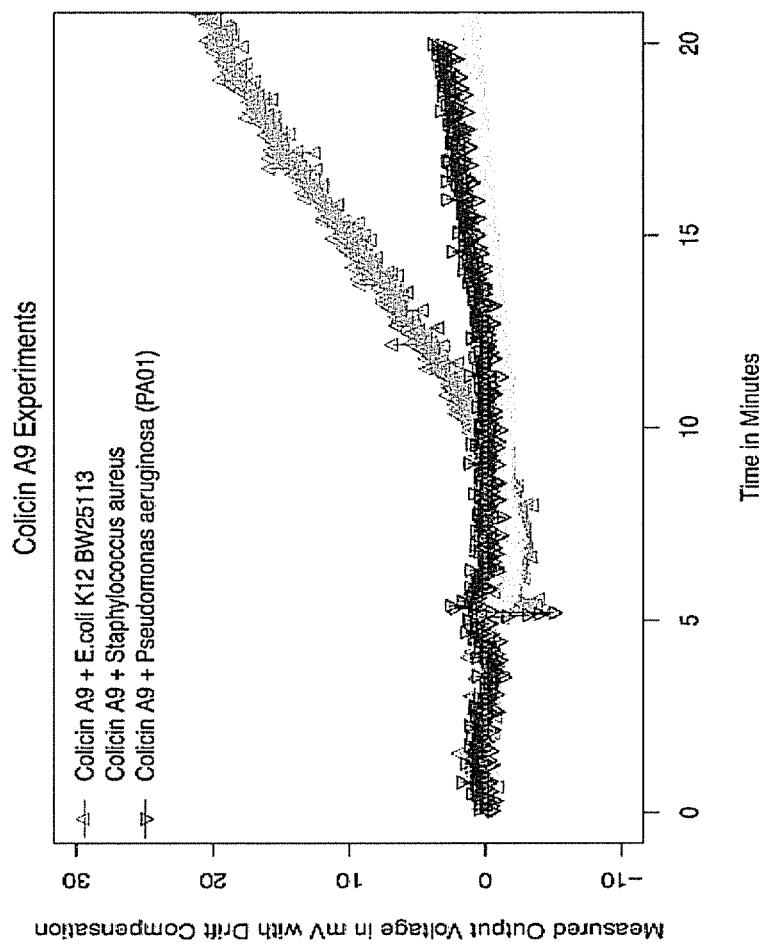
FIG. 10 shows additional experimental results of both positive and negative control experiments using the bacteria sensing system, in accordance with an example embodiment of the disclosure.

FIG. 10 shows the results of both positive and negative control experiments. As indicated, the integrated potassium-sensitive chip can detect the presence of the specific *E. coli* strain K12 BW25113 using the bacteriocin Colicin A9. As shown, the output increases as a result of the efflux of potassium ions from cells in the positive control test, as compared to the negative controls.

Other contemplated examples of colicins that can be used instead of Colicin A9 above are Colicin K, Colicin E1, or Colicin B.

Example 3

This example demonstrates that lysostaphin can be used to detect the presence of a bacterium in a sample using methods and devices according to the present disclosure. In this example, the lysostaphin from *Staphylococcus simulans* was combined with *Staphylococcus aureus* 8325 as the positive control. As negative controls, lysostaphin from *Staphylococcus simulans* was combined with *E. coli* K12 BW25113, and lysostaphin from *Staphylococcus simulans* was combined with *Pseudomonas aeruginosa* (PA01).

Figure 11:
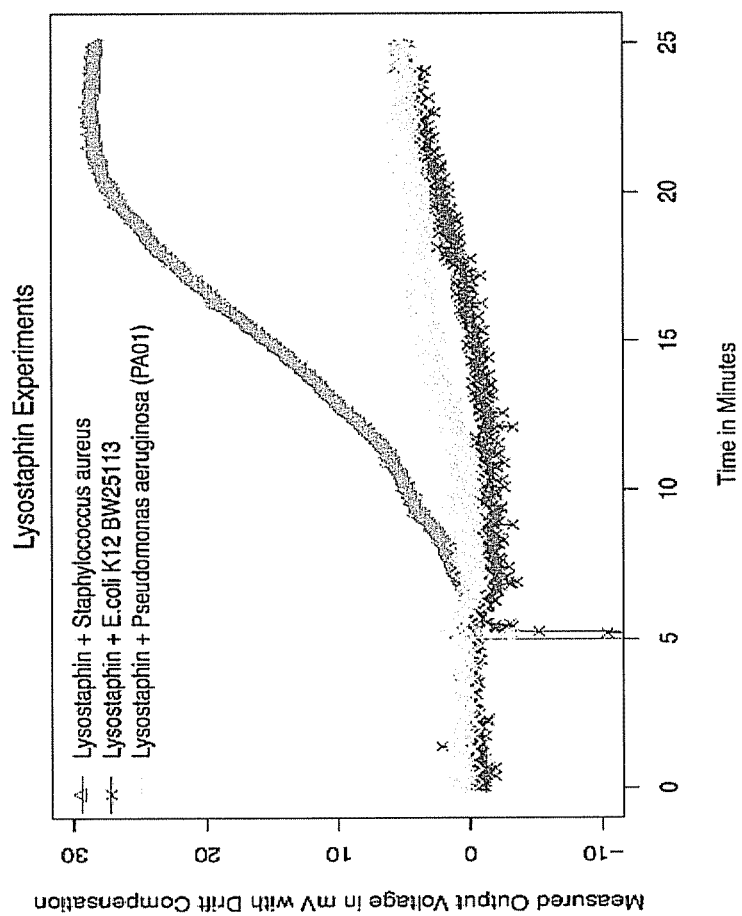
FIG. 11 shows additional experimental results of both positive and negative control experiments using the bacteria sensing system, in accordance with an example embodiment of the disclosure.

FIG. 11 shows the results of both positive and negative control experiments. As indicated, the integrated potassium-sensitive chip can detect the presence of the specific bacterial strain *Staphylococcus aureus* 8325 using the lysostaphin from *Staphylococcus simulans*. As shown, the output increases as a result of the efflux of potassium ions from cells in the positive control test, as compared to the negative controls.

Example 4

This example demonstrates that antibiotics can be used to detect the presence of a bacterium in a sample using methods and devices according to the present disclosure. In this example, the Polymyxin B antibiotic (PMB) was combined with E. coli K12 BW25113 in SM buffer as the positive control. As the negative control, Polymyxin B antibiotic (PMB) combined with E. coli K12 BL21 (DE3-.DELTA.tail) (referred to as BL21) in SM buffer. Experiments were performed as described above for Example 1, using the ISFET system 600.

Figure 12:
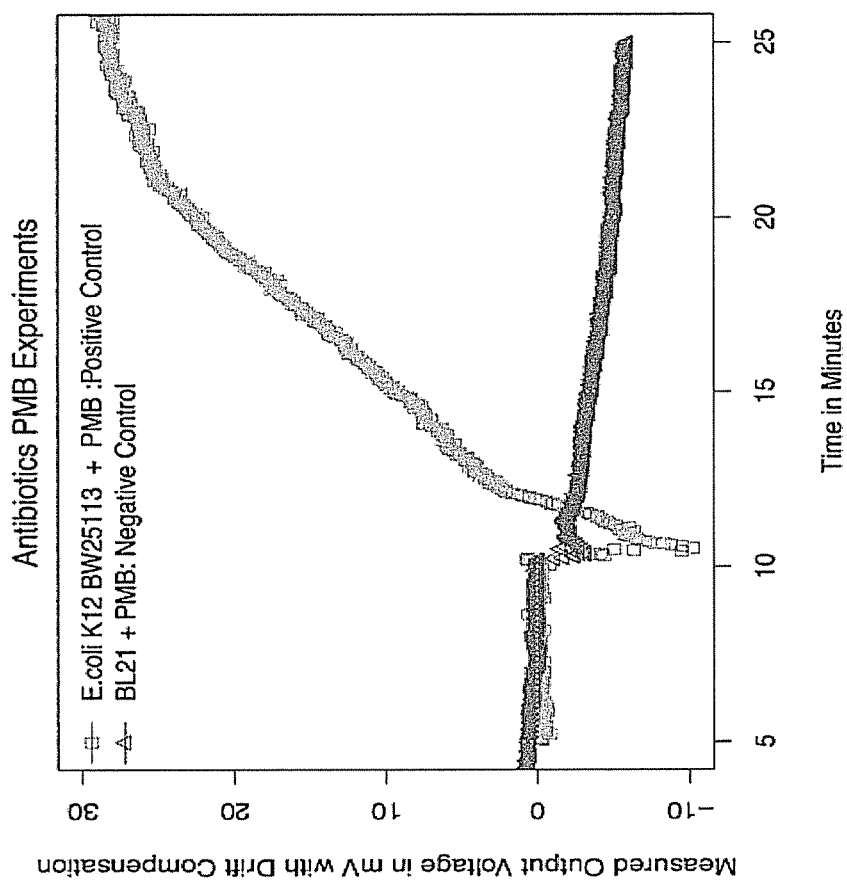
FIG. 12 shows additional experimental results of both positive and negative control experiments using the bacteria sensing system, in accordance with an example embodiment of the disclosure.

FIG. 12 shows the results of both positive and negative control experiments. As indicated, the integrated potassium-sensitive chip can detect the presence of the specific bacterial strain E. coli K12 using the Polymyxin B antibiotic (PMB). As shown, the output increases as a result of the efflux of potassium ions from cells in the positive control test, as compared to the negative control.

Figure 13C:
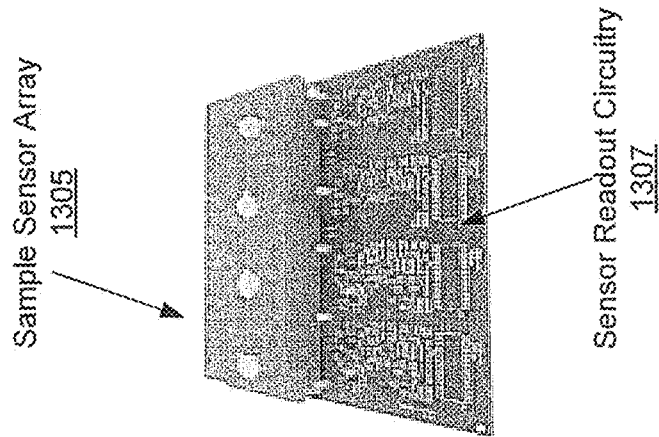
FIGS. 13A-13C illustrate applications for ISFET-based bacteria sensors, in accordance with an example embodiment of the disclosure.
Figure 13B:
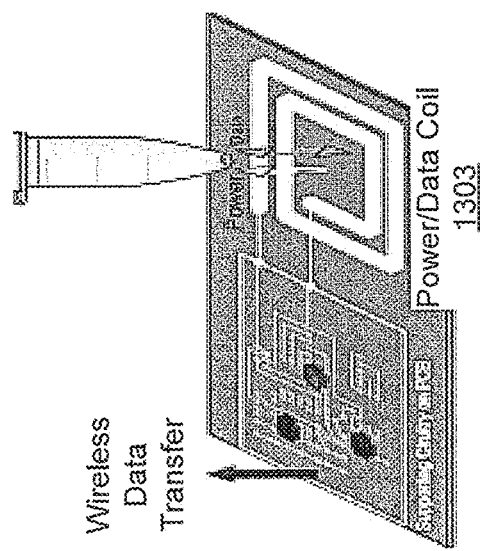
Figure 13A:
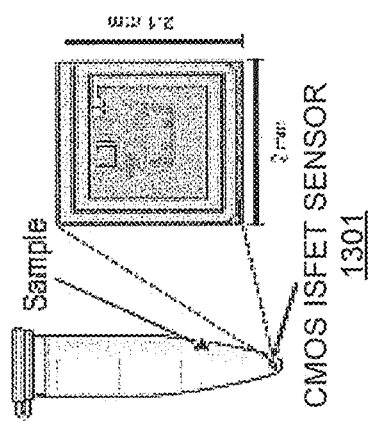

FIGS. 13A-13C illustrate applications for ISFET-based bacteria sensors, in accordance with an example embodiment of the disclosure. Referring to FIG. 13A, there is shown a CMOS ISFET sensor 1301 placed in a sample container, which may comprise a microcentrifuge tube, for example, although other sample container types may be utilized. The CMOS ISFET sensor 1301 may be encapsulated entirely except for sensor surfaces, and when placed in a sample container, may be exposed to the sample for measurement.

FIG. 13B illustrates a wireless power transfer from a reader to a CMOS sensor in contact with analyte. In addition, data may be transferred between (to and/or from) the CMOS ISFET sensor 1301 and the reader utilizing the same wireless power link or an auxiliary near-field wireless link In addition, a sample sensor array 1305, shown in FIG. 13C, may comprise CMOS ISFET sensors placed in an array of sample containers, with wireless data transfer to a circuit board with sensor readout circuitry 1307, thereby enabling the simultaneous testing of a plurality of samples, for example. In the example shown in FIG. 13C, four microcentrifuge tubes may be placed in a tube rack with wireless coupling to the sensor readout circuitry 1307.

Accordingly, one aspect the present disclosure relates to a sensor for detecting the presence of different bacterial strains in a sample by detecting the permeabilization of the bacteria cell wall by one or more antibacterial agents. Another aspect the present invention relates to a sensor for determining or estimating the concentration of different bacterial strains in a sample by detecting the permeabilization of the bacteria cell wall by one or more antibacterial agents. In some embodiments, the sensor includes antimicrobial agents, integrated ISFETs, possible additional ion-selective membranes, ISFET reading circuits, amplifiers, possible analog-to-digital converters and analog/digital processors. The presence of antimicrobial agents results in bacteria cell wall permeabilization and the release of intracellular ions into the environment. The integrated ISFET and possible additional ion-selective membranes integrated with ISFET reading circuits, amplifiers, and analog-to-digital converters detect the presence of the released ions in the sample. In still further embodiments, the processor is electrically connected to the system to analyze the signal and provide the output reading.

In some embodiments the antibacterial agent includes at least one bacteriophage, at least one phage ghost, at least one phage tail-like bacteriocin (PTLB), at least one antimicrobial peptide, at least one bacteriophage lytic enzyme, at least one bacterial lytic enzyme, at least one antibiotic, bactericidal antibiotic, or combinations thereof. In some embodiments the permeabilization of the cell wall is permanent, while in other embodiments the permeabilization is transient.

In various embodiments of the disclosure, the system comprising the ISFET, ISFET reading circuits, amplifiers, possible analog-to-digital converters and analog/digital processors are implemented to identify the efficacy of the antibiotic on the unknown sample containing possible bacteria. The bactericidal antibiotics if effective on the sample results in ion efflux from sensitive bacteria cells that can be detected by the system.

In various embodiments of the disclosure, the ISFET and supporting circuitry and processors are all integrated in a conventional integrated circuit fabrication processes like a CMOS fabrication process.

In various embodiments of the disclosure, an external reference electrode defines the voltage of the sample liquid. In various other embodiments the reference electrode can is integrated on the same substrate as the ISFET, reading circuitry and processors.

In various embodiments of the disclosure, the system comprises of differential and/or pseudo-differential ISFETs and ISFET circuitry and a metal as the reference electrode for complete integration. In some embodiments, the ion-selective membrane is deposited on one ISFET and the ion-insensitive membrane or no membrane is deposited on another ISFET in the differential/pseudo-differential pair. Both ISFETs are connected to their respective circuitry. In some embodiments of the disclosure both outputs are connected to difference amplifiers to measure the difference between the signals. This configuration makes the system completely integrated without use of external reference electrodes or non-standard integration of reference electrodes. It also helps with common-mode noise and compensation for circuit and system non-idealities.

In various embodiments of the disclosure, the ISFETs are made using different ion-selective membranes on their electrodes to detect different ion-concentrations released due to cell wall permeabilization.

In various embodiments of the disclosure, the processor comprises calibration circuitry on the same substrate as the ISFET to compensate for circuit and system non-idealities like mismatch and drift.

In various embodiments of disclosure, calibration of the ISFET non-idealities like DC mismatch and drift is performed by applying the sample containing possible bacteria in the first short time interval, recording the output DC and drift and other non-idealities. In the next interval the anti-microbial detection elements are added to the system. The calibration unit in the processor easily records the non-idealities in the first time interval and compensates for them in the second time interval. In some embodiments, a reference solution is applied to the system first for calibration.

In various embodiments of the disclosure, optimal detection and estimation algorithms can be implemented inside the processor.

In various embodiments of the disclosure the detection and estimation algorithms may utilize estimation of the slope of ISFET output voltage over time.

In some embodiments an array of ISFETs with different electrode sizes and possibly different ion-selective membranes are all integrated on the same substrate to detect different ion effluxes in the sample. The antimicrobial detection agents can be immobilized on ISFETs to detect different bacteria species in the sample. The array of the ISFETs can be integrated on the same substrate with their respective reading circuitry, amplifiers and processors.

In some embodiments an array of ISFETs with different electrodes having one or multiple bacterial strains are immobilized on top of the electrodes to test the efficacy of antimicrobial agents like bactericidal antibiotics on a sample.

In some embodiments the substrate comprises a first substrate and a second substrate and the at least one electrode are integrated on the first substrate and the ISFET and ISFET reading circuits and amplifier are integrated on the second substrate. In some embodiments, the processor is integrated on the second substrate. In various embodiments of the disclosure, the substrate comprises a first substrate and a second substrate and a third substrate. At least one electrode is integrated on the first substrate and the ISFET reading circuitry and analog blocks are integrated on the second substrate and digital processors and other digital circuits are integrated on the third substrate.

While the disclosure addresses various embodiments, it is not intended that the disclosure be limited to such embodiments. On the contrary, the disclosure encompasses various alternatives, modifications, and equivalents, as will be appreciated by those of skill in the art.

The invention claimed is:

1. A method for detecting a bacterium in a sample, said method comprising: providing a sample; contacting said sample with an integrated bacteria identification sensor and an antibacterial agent causing bacterial lysis and the efflux of potassium ions from said bacterium; and detecting a gate source voltage signal produced from said efflux of potassium ions from said bacterium; wherein an increasing gate source voltage signal over time is an indication that bacteria are present in said sample; and wherein said bacteria identification sensor comprises a potassium-sensitive ion-sensitive field-effect transistor (ISFET) having a passivation layer comprising $Si_3N_4$.

2. The method of claim 1 wherein said antibacterial agent is a bacteriophage.

3. The method of claim 1 wherein said antibacterial agent is a bacteriophage tail-like bacteriocin.

4. The method of claim 1 wherein said antibacterial agent is a lytic enzyme.

5. The method of claim 1 wherein said antibacterial agent is a bacteriophage ghost.

6. The method of claim 1 wherein said antibacterial agent is an antibiotic.

7. The method of claim 1, wherein said ISFET is coupled in a drain source follower configuration.

8. The method of claim 1, wherein said ISFET comprises a p-channel metal-oxide semiconductor (PMOS) transistor coupled to an electrode covered by the passivation layer, said passivation layer covered by a potassium-sensitive membrane.

9. The method of claim 1, wherein said bacteria identification sensor comprises a first complimentary metal-oxide semiconductor (CMOS) transistor with a potassium sensitive membrane and a second CMOS transistor with a potassium insensitive membrane.

10. The method of claim 9, wherein said first and second CMOS transistors are integrated on a single chip and coupled in a differential arrangement.

11. The method of claim 9, wherein gate terminals of said first and second CMOS transistors are coupled to a common electrode on said chip.

12. The method of claim 1, wherein said bacteria identification sensor comprises an array of ISFETS.

13. A method for detecting a bacterium in a sample, said method comprising: providing a sample having a bacterium; permeabilizing said bacterium by an antibacterial agent; and detecting a gate source voltage signal produced from the efflux of potassium ions using an integrated bacteria identification sensor comprising a potassium-sensitive ISFET having a passivation layer comprising $Si_3N_4$.

14. The method of claim 13, wherein said antibacterial agent is a bacteriophage.

15. The method of claim 13, wherein said antibacterial agent is a bacteriophage tail-like bacteriocin.

16. The method of claim 13, wherein said antibacterial agent is a lytic enzyme.

17. The method of claim 13, wherein said antibacterial agent is a bacteriophage ghost.

18. The method of claim 13, wherein said antibacterial agent is an antibiotic.

19. The method of claim 13, wherein said ISFET is coupled in a drain source follower configuration.

20. The method of claim 13, wherein said ISFET comprises a p-channel metal-oxide semiconductor (PMOS) transistor coupled to an electrode covered by the passivation layer, said passivation layer covered by a potassium-sensitive membrane.

21. The method of claim 13, wherein said bacteria identification sensor comprises a first CMOS transistor with a potassium sensitive membrane and a second CMOS transistor with a potassium insensitive membrane.

22. The method of claim 21, wherein said first and second CMOS transistors are integrated on a single chip and coupled in a differential arrangement.

23. The method of claim 21, wherein gate terminals of said first and second CMOS transistors are coupled to a common electrode on said chip.

24. The method of claim 13, wherein said bacteria identification sensor comprises an array of ISFETS.

* * * * *